United States Patent [19]

Nichols

[11] Patent Number: 4,704,254
[45] Date of Patent: Nov. 3, 1987

[54] FILTERED PORT SUITABLE FOR MEDICAL STERILIZATION CONTAINERS AND METHOD OR USE THEREOF

[76] Inventor: Robert L. Nichols, 808 Forth Worth, Jacksonville, Tex. 75766

[21] Appl. No.: 822,386

[22] Filed: Jan. 27, 1986

Related U.S. Application Data

[63] Continuation-in-part of Ser. No. 668,090, Nov. 5, 1984, Pat. No. 4,617,178.

[51] Int. Cl.$^4$ .......................... A61L 2/26; A61L 2/00
[52] U.S. Cl. .................................... 422/28; 206/363; 220/367; 422/26; 422/27; 422/292; 422/310
[58] Field of Search ................... 422/297, 292, 26, 27, 422/28, 300, 310; 206/363–365; 220/300, 367; 229/3.5 MR

[56] References Cited

U.S. PATENT DOCUMENTS

| | | |
|---|---|---|
| 3,437,423 | 4/1969 | Mohdradis . |
| 3,697,223 | 10/1972 | Kovalcik et al. . |
| 3,890,096 | 6/1975 | Nichol et al. . |
| 4,105,407 | 8/1978 | Sanderson .......................... 422/26 |
| 4,124,141 | 11/1978 | Armentroute et al. . |
| 4,154,342 | 5/1979 | Wallace .............................. 206/439 |
| 4,196,166 | 4/1980 | Sanderson et al. . |
| 4,251,482 | 2/1981 | Sanderson . |
| 4,271,973 | 6/1981 | Quagliaro et al. . |
| 4,372,921 | 2/1983 | Sanderson et al. . |
| 4,396,583 | 8/1983 | La Boeaf . |
| 4,402,407 | 9/1983 | Maly . |
| 4,416,417 | 11/1983 | Sanderson et al. . |
| 4,457,327 | 7/1984 | Pepper . |
| 4,458,705 | 7/1984 | Cawood . |
| 4,512,498 | 4/1985 | Leibinger . |
| 4,551,311 | 11/1985 | Lorenz . |

FOREIGN PATENT DOCUMENTS

| | | | |
|---|---|---|---|
| 152544 | 11/1984 | European Pat. Off. ............ | 422/292 |
| 2,839,219 | 3/1980 | Fed. Rep. of Germany ...... | 206/439 |
| 2542200 | 9/1984 | France ................................ | 422/297 |

Primary Examiner—Barry S. Richman
Assistant Examiner—William R. Johnson
Attorney, Agent, or Firm—Jerry W. Mills; Jefferson Perkins

[57] ABSTRACT

One or more ports (34) are formed in a bottom wall (18) of a housing (12) and/or a lid (14) of a medical instrument sterilization container (10). As formed in bottom wall (18), the port (34) includes a circumferential, downwardly tapering side member (42) that extends to a bottom member (40) having a plurality of orifices (44) to communicate a sealed interior (26) with the exterior. A filter cartridge (36) is provided for insertion in the port (34) and has a filter medium (60) that permits the passage of sterilizing gas or steam but does not permit the passage of contaminants. A side member (54) of the cartridge (36) tapers downwardly and inwardly from its perimeter to the filter medium (60) and is adapted to sealingly register with the port side member (42). A retainer (38) may be provided for keeping the cartridge side member (54) in sealing registration with the port side member (42).

21 Claims, 7 Drawing Figures

FILTERED PORT SUITABLE FOR MEDICAL STERILIZATION CONTAINERS AND METHOD OR USE THEREOF

RELATED APPLICATIONS

This application is a continuation-in-part of pending application Ser. No. 668,090, filed Nov. 5, 1984, now U.S. Pat. No. 4,617,178 issued Oct. 14, 1986.

TECHNICAL FIELD OF THE INVENTION

This invention relates to filters for sterile environments, and more particularly relates to filter ports in sterilization containers.

BACKGROUND OF THE INVENTION

It is necessary in hospital and other medical environments to sterilize medical instruments with steam or ethylene oxide. Various types of sterilization containers for such medical instruments have heretofore comprised muslin wraps, various paper wraps and sterilization containers. When using the various types of wraps, medical instruments are placed in a tray, wrapped by a recommended procedure, taped, labeled and placed in a steam or ethylene oxide sterilizer. The steam or ethylene oxide penetrates the wrap and kills the bacteria. Disadvantages in the use of the sterilization wraps include the repeated expenses of the disposable wraps, potential punctures of wrapping materials thereby causing contamination, limited shelf life of the wrapped instruments and the fact that the wraps are not stackable.

Various sterilization containers have been heretofore proposed which provide a hermetically sealed container with various filters. The filters on most of these conventional containers are provided with a spring steel plate, slightly bowed with clips. The filter medium, made out of sheet stock, lies in the bottom of the sterilization container, the plate then being pressed onto the bottom and clips attached. The filter medium thus acts as a gasket with pressure being applied from the plate. As the spring steel plates are repeatedly used, the clips wear, giving the plate a loose fit into the port and a defective seal.

Other conventional sterilization containers employ a plastic cartridge that has a ring snapping over a skirt to make the seal and a retaining ring which locks into place in order to secure the cartridge to the skirt. This snap-ring system will also obviously cause a great deal of wear to the components, thereby decreasing component life and increasing the danger that no seal will be formed.

A further plastic cartridge filter system has been proposed which is in part the subject of my parent application Ser. No. 668,090. The parent application discloses a single port disposed in the container lid and a pair of ports disposed in the container bottom. Each port has a filter cartridge adapted to be fit into the port and a retainer that holds the port into place. The port has an outer member with a plurality of orifices communicating the sealed volume to the exterior. The filter cartridge has a cylindrical side member, which meets with a cylindrical side member of the port, and an inwardly extending lower annular lip member across which a filter medium is extended. The filter medium allows the passage of such gases as ethylene oxide and steam but does not allow the passage of contaminants.

A retainer ring for this system has a cylindrical side member that clamps the cartridge in place through the aid of a plurality of tabs disposed around the perimeter of the retainer ring. These tabs engage with upstanding catch members by sliding underneath laterally extending flange members. The flange members exert downward pressure on the tabs, which in turn communicate their downward pressure to the cartridge filter to make a seal.

While this port, filter, and retainer system has proven advantageous over prior art sterilization container filters, certain problems have revealed themselves. A principal problem inheres from the cylindrical design of the port, the cartridge filter and the retaining member. None of the cylindrical walls are involved in providing an adequate container seal. The sealing function is instead performed by the contact of a lower annular lip member of the cartridge with a lower annular lip member of the recessed port. The cartridge also has an upper, outwardly extending annular lip member which may make contact with the general interior surface of the container wall at the same time or even before contact of the cartridge's lower annular lip member with the annular lip member of the recessed port. Thus, the needed pressure to be exerted between the cartridge and the port annular lip member may be partially diverted to the contact between the upper cartridge annular lip member and the interior surface, to the degradation of the seal.

The retainer ring heretofore employed is also generally cylindrical in shape with an upper outwardly extending annular lip member and a lower inwardly extending annular lip member. The downward force exerted by the retaining member may be distributed along both lip members or even only on the upper lip member, thereby limiting or entirely negating any downward force to be applied between the lower annular lip member of the cartridge and the port annular lip member. This again causes problems in the quality of the seal.

Since the recessed port, cartridge and retainer ring of the prior filter are cylindrical, a substantial drag develops in inserting and removing the cartridge from the recessed port, and a like drag occurs in removing the retainer ring from the upper and inward surfaces of the filter cartridge. Both of these drags produce sources of wear that limit the effective life of both the sterilization container and the retainer ring.

In order to insure a proper seal, it has heretofore been necessary to construct filter cartridges out a relatively thick and rigid plastic. Such a thick, rigid plastic cartridge has also heretofore been necessary because a thinner or less rigid plastic would soften and leak at critical locations when subjected to hot steam, thus breaching the sterile interior of the container. A thick, rigid plastic cartridge is of course significantly more expensive than one made of thin plastic, and the rigid plastic has a lesser ability to conform to imperfections of the mating, sealing members.

A further problem with the unimproved cartridge, retainer and port system is that some difficulty is encountered in getting the tabs underneath the inwardly projecting flange portions when securing the filter to the port with the retainer ring. Further, the technician does not absolutely know how far to turn the retainer ring so that the tabs are underneath the flange portion, and there is a danger that the tabs will be rotated such that they become free on the other side of the flange portions.

A need has therefore arisen to provide a retainer and filter cartridge system that provide for a more effective seal while at the same time preventing wear to the various filter system components and controlling costs of manufacture. A need has also arisen to improve the cartridge and retainer securement means so that the retainer ring and the filter cartridge it secures can be easily positioned.

SUMMARY OF THE INVENTION

In accordance with one inventive aspect of the present invention, a medical instrument sterilization container includes at least one port disposed in a rigid wall portion of one or more of the walls or lid of the sterilization container. As formed in a bottom wall of such a container, the filter port has a peripheral side member that tapers downwardly from an upper perimeter on the interior container surface to a lower member having a plurality of orifices for the communication of the sealed interior of the container to the exterior. A filter cartridge having a tapered side member is adaptable to sealingly register with the port side member. The filter cartridge has a filter extending across a bottom member of it. When being inserted into the port, the filter cartridge side member sealingly registers with the port side member, before or at least simultaneously with the contact of any other filter cartridge portion with any other port or interior container surface portion.

In accordance with another aspect of the invention, a retainer ring for the securement of the filter cartridge into the port has a tapered side member that is adaptable to register with an interior tapered surface of the filter cartridge side member. In this manner, an outward and downward circumferential force is evenly and efficiently distributed to the filter cartridge side member, pressing it against the port side member to make a perfect seal superior to the more usual horizontal "gasket compression" type seals. Preferably, the retainer ring side member registers with the inward surface of the filter cartridge side member before or at least simultaneously with the contact of any other portion of the retainer ring with the filter cartridge.

In a further aspect of the invention, the retainer ring has a plurality of laterally radially extending tabs, each tab having an at least partially beveled or tapered leading edge and a thickened stop member on a trailing edge. The tabs are adapted to be rotated underneath inwardly projecting flange portions of upstanding catch members formed around the port, the bevels making it easy to slip the tabs underneath the flanges. The thickened stop members provide a positive stop so that the retainer is not rotated to the point that the catch member no longer secures it.

In accordance with yet a further aspect of the invention, a new filter cartridge has been provided with a thin, relatively flexible plastic side member that forms an improved seal with the port and the retainer ring and provides a reduction in manufacturing costs.

The filtered port cartridge and retainer of the invention are preferably formed or provided for in both a bottom wall and in a lid of a sterilization container, the orientation of the port, cartridge and retainer formed in the lid being reversed from a filtered port formed in the container bottom wall. Although the filtered port has been provided specifically for use with a medical instrument sterilization container, it can be employed in any instance where a gas is desired to be filtered into or out of a volume through a gas-impermeable partition having a rigid portion.

Other aspects of the invention will become apparent from the description that follows.

BRIEF DESCRIPTION OF THE DRAWING

For a more complete understanding of the present invention and the objects and advantages thereof, reference is now made to the following description taken in conjunction with the accompanying drawings in which.

DETAILED DESCRIPTION OF THE INVENTION

Figure 1:
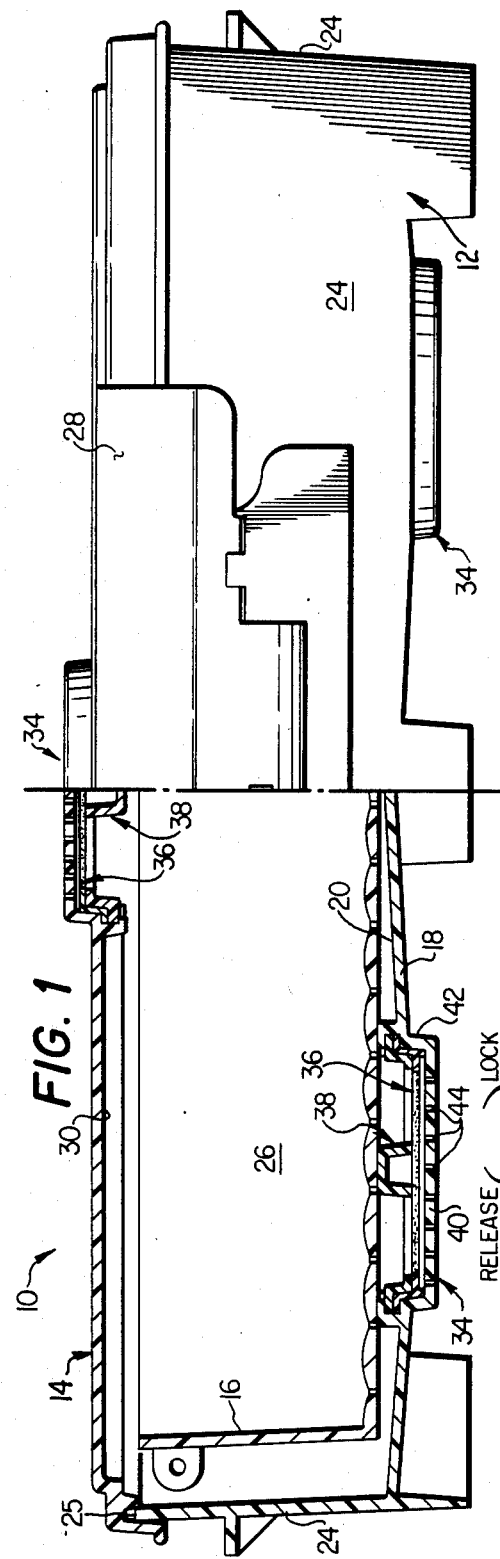
FIG. 1 is a part sectional and part front elevational view of a sterilization container incorporating the filtered port of the invention, showing the lid in a closed, sealed position, lid and bottom filter cartridges of the invention being secured in place in ports in the container.

Referring to FIG. 1, a sterilization container 10 incorporating the invention includes a housing 12 and a removable lid 14. A removable tray 16 is received within housing 12 and is adapted to receive various medical instruments such as knives, scissors and the like. Housing 12 has a bottom wall 18 with an interior surface 20. Housing 12 further includes a plurality of side walls 24 extending upwardly from bottom wall 18.

Suitable sealing surfaces 25 are provided between side walls 24 and lid 14 in order to substantially hermetically seal interior 26. In the illustrated embodiment, a plurality of metal clamps 28 (one shown) are attached on opposed side walls 24 and are manually moveable in order to clamp lid 14 to housing 12. Lid 14 has a general flat interior surface 30.

Although the sterilization container shown in the illustrated embodiment is rectangular in shape, it can be of any convenient shape, such as an oval or circular shape, in which case there would be one continuous side wall.

Ports 34 are formed into a rigid portion of a wall of housing 12 and/or into a rigid portion of lid 14, so that steam, ethylene oxide or other sterilizing gaseous medium can pass from the exterior into interior 26 to sterilize the instruments situated therein. Preferably, at least one port 34 is disposed in lid 14, and two ports 34 are disposed in bottom wall 18. In this way, a flow-through of the sterilizing gas can be achieved and if steam is used, steam condensate can exit the container through bottom ports 34. It is preferred that walls 18–24 and lid 14 be constructed of relatively rigid material. All of the elements of sterilization container 10 herein described should, of course, be constructed of materials that can withstand the pressures, temperatures and sterilizing media to be employed in the sterilization process. More particularly, they should withstand, in the case of a steam sterilization cycle, the effects of steam at elevated temperatures and pressures.

Instead of or in addition to the dispositions of ports 34 in lid 14 and bottom wall 18 as illustrated, one or more ports 34 could be disposed in side walls 24.

Figure 2:
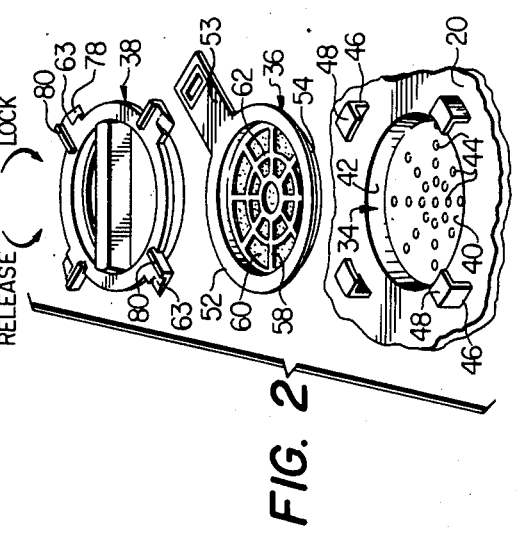
FIG. 2 is an exploded view of a filter port, a filter cartridge and a retainer ring of the invention.

Referring to FIG. 2, a preferred embodiment of a port 34 is illustrated, together with a corresponding filter cartridge 36 and a retainer 38. Each of ports 34 is similar in construction to the remaining ports 34, and it is preferred that ports 34 be identical. Therefore, only one of the bottom ports 34 will be described in detail. It should be understood that in the following description of a bottom port 34, terms such as, "bottom", "top", "over", "under", "lower" and "upper" should be reversed in applying the description to a port 34 that is disposed in lid 14. As hereinafter used in the specification and claims, "top", "over" and "upper" denote a direction or placement toward or close to interior 26, and "bottom", "under" and "lower" denote a direction or placement toward or close to the exterior of container 10.

As shown in FIGS. 1 and 2, port 34 comprises a bottom or outer member 40 that, together with a circumferential side member 42, defines a depression below the general interior surface 20 of bottom wall 18. It is preferred that port 34 be circular in shape, although any other shape may suffice, such as a polygonal or irregular shape, so long as cartridge 36 has a corresponding shape. Side member 42 of port 34 tapers downwardly and inwardly from the general interior surface 20 of bottom wall 18 to bottom member 40. Port side member 42 is preferably formed of a rigid, impervious material such as relatively hard plastic and is dimensioned so as to be relatively thick to present a relatively rigid surface. A plurality of orifices 44 perforate bottom member 40 in order to allow gas to pass from the interior 26 to the exterior, or vice versa.

A plurality of upstanding catch members 46 are uniformly distributed about port 34, and are preferably radially equidistant from port 34 and angularly equidistant from each other. A flange 48 extends inwardly from the upper portion of each catch member 46.

Filter cartridge 36 is dimensioned to be closely received into port 34. With the exception of filter medium 60 (later described), filter cartridge 36 is preferably integrally molded out of a more resilient, deformable material than the materials forming port 34 or retainer 38. The softer plastic forming cartridge 36 must still withstand the operating temperatures, pressures and sterilizing media to be employed. Filter cartridge 36 is circular in shape and includes, a top lip member 52 that laterally and circumferentially extends outwardly beyond the limits of port side member 42 when cartridge 36 has been inserted into port 34. A handle 53 extends outwardly from lip member 52. A preferably frustoconically-shaped cartridge side member 54 tapers downwardly from the top lip member 52. A bottom lip member 56 (FIG. 3) extends circumferentially and laterally inwardly from cartridge side member 54 at a point close to or at its bottom.

Filter cartridge 36 further has cross members 58 that extend from and across bottom lip member 56. In combination with bottom lip member 56, cross members 58 provide support for filter medium 60 which extends over the bottom of cartridge 36. Further support and protection for filter medium 60 may be provided by one or more concentric circular members 62 that are preferably integrally formed with cross members 58. Filter medium 60 extends completely across the open interior area left by bottom lip member 56, and is sealably attached thereto in a manner later described. Filter medium 60 can be fashioned of any suitable commercially available material which allows the passage of sterilizing gas through it, and, in the case where the sterilizing gas is steam, which further allows the passage of condensate, but which at the same time does not allow the passage of bacteria and other contaminants through it. Preferably, filter medium 60 is fabricated from a nonwoven synthetic fabric.

A retainer member 38 is provided to secure filter cartridge 36 in place in port 34. In the illustrated embodiment, retainer 38 is made of a rigid, thermally resistant material, such as hard plastic, and is dimensioned to be relatively thick for rigidity. Retainer 38 has a plurality of radially extending fins or tabs 63 disposed angularly equidistantly about its periphery. Each tab 63 is disposed to engage a corresponding upstanding catch member 46 when retainer 38 is securing cartridge 36 in place.

Figure 3:
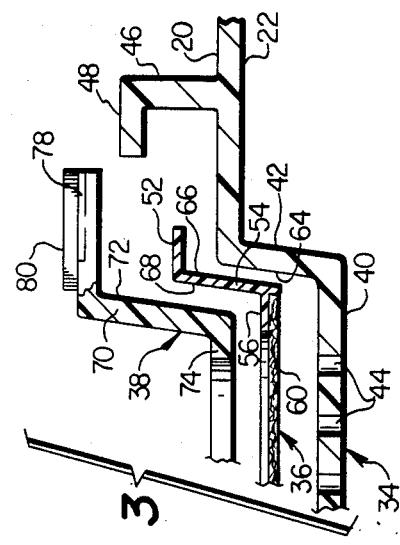
FIG. 3 is an exploded sectional view of the port, filter cartridge and retainer ring shown in FIG. 2, showing the relationship of the port, filter cartridge and retainer ring side wall members.

Referring now to FIG. 3, the structural relationship between port 34, filter cartridge 36 and retainer 38 is more particularly shown in an exploded view. Port side member 42 is preferably frustoconical in shape, and tapers downwardly from the general interior surface 20 of bottom wall 18 to bottom member 40. Port side member 42 has an interior surface 64 that preferably has a uniform slope. Cartridge side member 54 has a radially exterior surface 66 and an opposed interior surface 68. An important aspect of the invention is that the taper or slope of any given point of cartridge side member exterior surface 66 matches the taper or slope of a corresponding point on port side member interior surface 64. In this manner, when cartridge 36 is fitted into port 34, the entire exterior surface 66 of cartridge side member 54 will sealably engage with interior surface 64 of port side member 42 to provide the most efficient seal possible. At the same time, since the degree of slope is preferably the same throughout the circumference and depth of cartridge side member 54 and port side member 42, all points of exterior surface 66 will contact all points of interior surface 64 substantially simultaneously, thereby preventing all but a minimum of drag and wear upon the insertion or extraction of filter cartridge 36 into or from port 34.

Retainer 38 preferably has a side member 70 with a frustoconical exterior surface 72. Exterior surface 72 preferably has a uniform downward or inward slope or taper throughout its circumference and depth, which taper preferably matches the taper of interior surface 68 of cartridge side member 54. In this way, a uniform circumferential pressure can be applied to side member 54, and only a minimum of wear and drag occurs each time retainer 38 is secured in place or removed.

Figure 4:
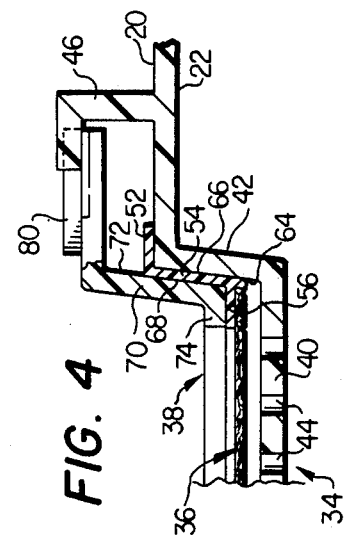
FIG. 4 is a sectional view of the port, filter cartridge and retainer ring of FIGS. 2 and 3 shown in an assembled position.

Referring to FIG. 4, port 34, cartridge 36 and retainer 38 are shown in assembled position. In the illustrated embodiment, retainer side member 70 is shown squeezing cartridge side member 54 against port side member 42. A further important aspect of the invention is that, when cartridge side member 54 is in complete sealing engagement with port side member 42, cartridge bottom lip member 56 and filter medium 60 will be spaced from port bottom member 40. This insures that the entire sealing pressure applied by retainer 38 onto cartridge side member 54 is not dissipated to bottom member 44. Likewise, upper lip member 52 of cartridge 36 does not engage the general interior surface 20 of the bottom wall 18 until cartridge side member exterior surface 66 is in complete sealing engagement with port side member interior surface 64.

In the illustrated embodiment, retainer 38 further includes a bottom lip member 74 that is circumferential and extends radially inwardly. It is preferred that bottom lip member 74 not contact cartridge bottom lip member 56, if at all, until retainer side member exterior surface 72 is completely engaged with cartridge side member interior surface 68. In this way, the squeezing force applied by retainer 38 to cartridge side member 54 is not dissipated onto lip member 56. The described sequence of surface contacts when cartridge 36 is being seated and then secured in place in port 34 insures that the seal developed between cartridge side member 54 and port side member 42 is the best possible. The wedge-like frustoconical seal between the cartridge and port side members 54 and 42 of the invention is superior to the conventional flat, gasket-type seal.

Figure 4A:
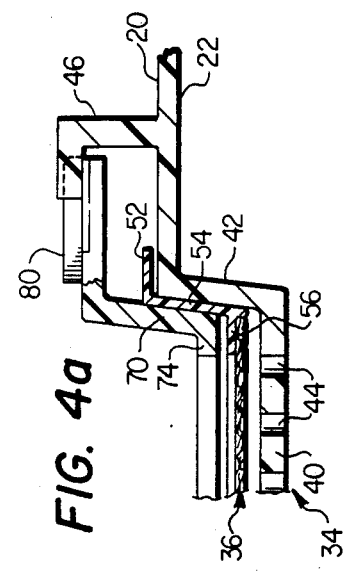
FIG. 4a is an alternate embodiment of the assembled port, filter cartridge and retainer ring shown in FIG. 4, showing small spaces between annular lip members of the retainer ring, filter cartridge and the general interior surface of the housing.

FIG. 4 shows an embodiment wherein upper cartridge lip member 52 makes contact with the general interior surface 20 of bottom wall 18 simultaneously with the firm, sealing engagement of cartridge side member 54 with port side member 42. Likewise, bottom retainer lip member 74 engages with bottom cartridge lip member 56 at the same time that retainer side member exterior surface 72 makes a firm engagement with cartridge side member interior surface 68. However, these various horizontal surfaces do not have to make contact at all as shown in the alternate embodiment shown in FIG. 4a. Like FIG. 4, cartridge side member 54 is being squeezed between the frustoconical surfaces of retainer side member 70 and port side member 42. However, as can be seen, small spaces exist between retainer bottom lip member 74 and cartridge bottom lip member 56, as well as cartridge upper lip member 52 and interior surface 20.

Figure 5:
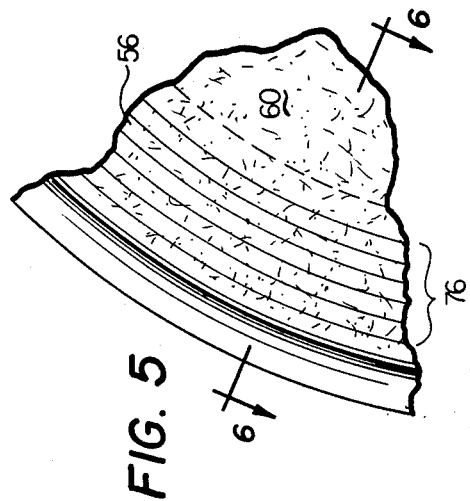
FIG. 5 is a partial bottom plan view of the filter cartridge shown in FIGS. 1–4a, showing the method of attachment of a filter medium to the cartridge.
Figure 6:
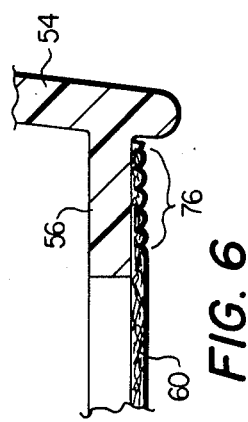
FIG. 6 is a partial side sectional view taken substantially along line 6—6 of FIG. 5.

FIGS. 5 and 6 are plan and sectional details of filter cartridge 36, respectively, showing the attachment of filter medium 60 to bottom lip member 56. As can be seen, a plurality of concentric bonding joints 76, preferably heat seals, are made between bottom lip member 56 and filter medium 60. The concentric arrangement of heat seals or bonds 76, which can be made through a high frequency heat bonding process, make sure that if the integrity of any one heat seal is breached, there will be several further intact heat seals preventing the escape of bacteria or other contaminants from one side of the filter medium to the other.

FIGS. 2-4 further illustrate how retainer 38 is used to affix cartridge 36 in place in port 34. Each tab 63, as is best illustrated in FIG. 2, has a leading beveled edge 78 that extends through at least a portion of the leading edge of tab 63, and a thickened portion or upstanding stop member 80 on its trailing edge. The leading and trailing edges of tabs 63 are substantially parallel to radii of retainer 38 drawn through them and are perpendicular to the generally circular perimeter of retainer 38. Each catch member 46 has a radially inwardly extending flange member 48 that is dimensioned to receive and hold down a corresponding tab 63. Cartridge 36 is first placed in port 34, and then retainer 38 is placed on top of and inside cartridge 36 such that tabs 63 are at different angular positions than corresponding catch members 46. Retainer 38 is then held down and rotated clockwise (or held up and rotated counter-clockwise in the case of fitting a cartridge 36 into a port 34 disposed in lid 14) until beveled edges 78 slide under flanges 48. The clockwise motion of retainer 38 is continued until upstanding catch members 46 make contact with thickened portions or upstanding stop members 80. This prevents the retainer 38 from being rotated so far that tabs 63 pop out on the other side of flanges 48.

In the secured position, retainer 38 applies an even, circumferential pressure to seal cartridge 36 to port 34. In removing cartridge 36 from port 34, the reverse procedure is employed.

In operation, cartridge members 36 are fitted into the various ports 34 in sterilization container 10, the frustoconical exterior surface 66 of each cartridge side member 54 sealably registering with a corresponding port side member 42.

Then, for each port 34, frustoconical exterior surface 72 of retainer side member 70 is brought into registry with the inwardly tapering interior surface 68 of cartridge 36. Downward force is then applied to retainer 38 in order to sealably squeeze cartridge side member 54 between port side member 42 and rigid retainer side member 70. Retainer 38 is then rotated until beveled edges 78 and tabs 63 slide under flange members 48 of upstanding members 46, the rotation continuing until upstanding members 46 make contact with corresponding thickened portions or stop members 80 of tabs 63.

After the filter cartridges 36 are in place, the medical instruments to be sterilized are to be deposited in tray 16, and the same is deposited in housing 12. Lid 14 is then secured to housing 12 in order to create sealed volume 26. The container and its contents are then subjected to a steam and/or ethylene oxide treatment to sterilize the medical instruments. After the sterilization treatment, the container and its contents may be stored in a sterilized condition for later use. When container 10 is opened and the medical instruments removed for use, it is preferred that cartridges 36 be removed and discarded and further cartridges 36 substituted to minimize contamination.

The invention herein described is not necessarily limited to application to medical instrument sterilization containers, but may be employed in any situation where it is desired to completely filter a gas from one volume or atmosphere through an otherwise gas-impermeable, and completely contaminant-impermeable, partition to a second atmosphere or gas volume. The system herein described provides a filtration system with a maximally effective seal of the filter element to the partition with a minimum of wear to the permanent sealing surfaces. The filter cartridge of the system is at the same time easily interchangeable, and as such, the system is conveniently adapted to the use of disposable filter cartridges.

Whereas the illustrated embodiment has been described in detail, it should be understood that various changes, alterations and substitutions can be made therein without departing from the spirit and scope of the invention as defined by the appended claims.

What is claimed is:

1. A method of sterilizing medical instruments in a container including the steps of:
   providing a housing dimensioned for receiving medical instruments;

fitting a disposable filter cartridge into at least one port in said housing, the step of fitting including:
  contacting and registering substantially all of an outward frustoconical surface of a side member of said cartridge filter with a substantially rigid frustoconical port side member;
  registering an upper cartridge lip extending from a peripheral shoulder of the cartridge side member with the interior surface of said housing;
  registering a substantially rigid frustoconical side member of a retainer against an inner frustoconical surface of the cartridge side member;
  disposing a shoulder formed from the retainer side member and force-applying means of the retainer substantially radially inwardly from the cartridge shoulder;
  disposing the cartridge shoulder radially inwardly from a shoulder formed from the port side member and the housing, such that sealing contact between substantially all of the contact surface and the port side member will be retained;
  applying force by the retainer to the cartridge against the port in order to sealably squeeze the cartridge side member between the port and retainer side member;
  securing the retainer to keep the cartridge side member in sealed registry with the port side member;
installing a cartridge filter in a lid for the housing using the same steps as the installation of a cartridge filter in the housing;
depositing medical instruments in the container;
securing the lid to the housing in order to create a sealed volume;
subjecting the container and its contents to a sterilization treatment;
opening the lid and removing the sterilized instruments for use;
removing the cartridges from said ports; and
replacing the cartridges with other cartridges in a manner similar to the installation of the replaced cartridges.

2. The method of claim 1, wherein the step of securing the retainer includes the following steps:
  rotating the retainer until a beveled edge on each of a plurality of tabs distributed around the periphery of the retainer slides under a corresponding catch member affixed to the container wall around the port; and
  further rotating the retainer ring until thickened stop members disposed on said tabs are stopped by the catch members.

3. A filtered port formed in a rigid portion of a gas impermemable wall of a medical sterilization container including at least one endless port side member tapering radially inwardly and axially away from said wall at an angle, said port comprising:
  a disposable filter cartridge for removable insertion in said port, said cartridge having a substantially planar filter that allows the passage of gas or stream therethrough but prevents the passage of contaminants therethrough, a substantially planar support member of said cartridge having an endless outer perimeter, said filter mounted exclusively on said support member, an endless side member of said cartridge having a contact surface and tapering radially outwardly and axially away from said outer perimeter at substantially said angle for sealing contact and registry with said port side member throughout substantially all of said contact surface.

4. The filtered port of claim 3, wherein:
  said port side member tapers from a port perimeter on said wall to a bottom member extending across said port, said bottom member having a plurality of orifices therethrough to communicate said port with the interior of said container;
  said cartridge having an outer lip formed on said side member;
  means for removably securing said cartridge having a continuous peripheral substantially rigid side member tapering at a taper substantially equal to the taper of said cartridge side member, said securing means operable to sealingly register with said cartridge side member to apply an even outward circumferential pressure to said cartridge to circumferentially seal said cartridge side member to said port side member.

5. The filtered port of claim 4, wherein said securing means, said cartridge side member and said port side member are frustoconical in shape.

6. The filtered port of claim 4, wherein said cartridge side member is thin and flexible relative to said port side member and said securing means, said securing means squeezing said cartridge side member against said port side member to form a circumferential seal between said cartridge and said port.

7. The filtered port of claim 4 wherein a seal is provided between said cartridge side member and said cartridge outer lip and the interior of said port side member and the interior of said gas impermeable wall.

8. The filtered port of claim 4, wherein:
  said filter is spaced from the bottom of said port when said cartridge side member is in sealed contact and registry with said port side member.

9. The filtered port of claim 4, wherein said securing means includes a plurality of circumferentially spaced tabs;
  a plurality of upstanding catch members disposed on said gas impermeable wall about the perimeter of said port, each said catch member operable to extend over a respective tab and exert force thereon to cause said securing means to exert a sealing circumferential pressure on said cartridge.

10. The filtered port of claim 9, wherein each said tab has a tapered leading edge and a thickened trailing edge;
  each said catch member including an upstanding portion protruding therefrom and a flange extending radially inwardly from said upstanding portion for extending over a respective retainer tab and exerting force thereon; and
  said tapered leading edge facilitating the rotation of said tab underneath said flange, said thickened trailing edge providing a stop against said catch member to limit rotational movement of said tab with respect to said catch member.

11. A sterilization container dimensioned for receiving medical instruments for sterilization by gas or steam, comprising:
  a plurality of walls including a top wall and a bottom wall, said walls defining a sealed volume;
  means for permitting access to said volume for the placement of medical instruments therein, said means sealingly engaging with at least one wall to maintain the sterility of said volume;

at least one port disposed in one of said walls of said container for the passage of gas therethrough, said port including an endless substantially rigid port side member tapering away and radially inwardly from said wall at an angle to form a depression; and a filter cartridge for removable insertion in said port, said cartridge having a filter passing gas therethrough but preventing the passage of contaminants into said volume, a substantially planar support member of said cartridge having an outer perimeter, said filter mounted exclusively on said support member, an endless side with a contacting surface, said side tapering radially outwardly and away from said perimeter at substantially said angle and dimensioned to sealingly contact and register with the interior of said port side member, the registry of said cartridge side with said port side member producing a minimum of drag and wear during insertion and removal of said cartridge, the sealing registry occurring for substantially all of the contacting surface of said cartridge side.

12. The sterilization container of claim 11, wherein said wall having said port disposed therein is formed in a removable top lid, said top lid sealingly engaging with at least one side wall of said container to maintain the sterility of said volume.

13. The sterilization container of claim 11, wherein said wall bearing said port comprises said bottom wall.

14. The sterilization container of claim 11, wherein said cartridge side and said port side member are frustoconical in shape.

15. The sterilization container of claim 11, wherein said side of said cartridge sealingly registers with said port side member before or during the contact of any other portion of said cartridge with said port.

16. The sterilization container of claim 15, wherein said cartridge further comprises an endless lip member extending laterally outwardly from said cartridge side and joined thereto at a cartridge shoulder, said lip member sealingly engaging with the interior surface of said wall simultaneously with or after the sealing registry of said cartridge side with said port side member, said port side member joined to said wall at a port shoulder, said cartridge shoulder disposed radially interiorly of said port side shoulder when said side and said side member are in registry to assure that said side and said side member remain in sealing contact through substantially all of the contacting surface of said side.

17. The sterilization container of claim 15, wherein said port side member is substantially rigid, said side of said cartridge being relatively flexible in comparison to said port side member.

18. The sterilization container of claim 17, wherein said cartridge is substantially thinner in cross-section than said port side member.

19. A sterilization container dimensioned for receiving medical instruments for sterilization by gas or steam, comprising:
a housing comprising a plurality of side walls and a bottom wall;
a removable lid for said housing for enabling access to said housing and for preserving a sterile sealed volume therein, said lid and said bottom wall having interior surfaces;
a plurality of ports formed in said lid and in said bottom wall;
each said port comprising a bottom member and a rigid frustoconcial side member tapering outwardly from a port shoulder on said bottom wall to said bottom member, said bottom member having a plurality of orifices therethrough to communicate said port with the interior of said container;
a filter cartridge adapted for insertion in said port and having a substantially planar support ring with an outer perimeter, a frustoconical side member of said cartridge formed on said perimeter and with a taper matching the taper of said port side member, said cartridge side member having a contact surface for sealingly contacting said port side member, an annular lip member extending laterally outwardly from a peripheral cartridge shoulder at one end of said cartridge side member, a filter disposed radially inwardly from said outer perimeter and sealably extending across said cartridge support ring opposite said one end to form a barrier against contaminants but allowing gas to pass therethrough;
a substantially rigid retainer for securing said filter cartridge in said port, said retainer having a frustoconical side member with a taper matching the taper of said port side member, a lip member of said retainer forming a peripheral shoulder at one end of said retainer side member, said retainer side member tapering radially inwardly from said end, means for applying a circumferential force against said cartridge side member and said port side member mounted on said retainer lip member, said retainer shoulder disposed substantially radially inwardly from said cartridge shoulder and said cartride shoulder disposed radially inwardly from said port shoulder;
said side member of said filter cartridge being retained within said port by said retainer, such that substantially all of said contact surface remains in sealing contact with said port side member.

20. The sterilization container of claim 19 and further comprising:
a plurality of retaining tabs equidistantly distributed around said lip member of said retainer and extending laterally outwardly therefrom, each said tab having leading and trailing edges substantially parallel to a radius of said retainer passing through said tab;
at least a portion of said leading edge having a beveled upper surface, said trailing edge having a thickened stop member; and
each said port having a plurality of catch members equal to said plurality of tabs, said catch members radially equidistantly distributed around said port perimeter, each catch member having an upstanding portion extending into said container from said interior surface, said upstanding portion having an upper end, a lateral portion extending radially inwardly from the end of said upstanding portion, said lateral portion adapted to slideably receive said tab leading edge and being further adapted to provide a stop against which said thickened stop member can engage in order to halt the rotation of said retainer with respect to said catch member.

21. The medical instrument sterilization container of claim 20, wherein each said port is substantially identical to each other said port, each said filter cartridge being useable in any of said ports.

* * * * *